(12) United States Patent
Alamin et al.

(10) Patent No.: US 7,935,136 B2
(45) Date of Patent: May 3, 2011

(54) FACET JOINT FUSION DEVICES AND METHODS

(76) Inventors: Todd F. Alamin, Woodside, CA (US); Uriel Hiram Chee, Santa Cruz, CA (US)

( * ) Notice: Subject to any disclaimer, the term of this patent is extended or adjusted under 35 U.S.C. 154(b) by 1590 days.

(21) Appl. No.: 11/155,077

(22) Filed: Jun. 16, 2005

(65) Prior Publication Data

US 2006/0004367 A1 Jan. 5, 2006

Related U.S. Application Data

(60) Provisional application No. 60/581,196, filed on Jun. 17, 2004.

(51) Int. Cl.
  *A61B 17/56* (2006.01)
  *A61B 17/70* (2006.01)
  *A61B 17/80* (2006.01)
  *A61B 17/81* (2006.01)
  *A61F 2/44* (2006.01)

(52) U.S. Cl. .......... 606/279; 606/74; 606/246; 606/247; 606/280; 606/281; 623/17.11

(58) Field of Classification Search ............ 606/74, 606/246–248, 232, 139, 279, 225, 262–263; 411/999; 24/703.1, 17 R, 18, 17 B, 30.5 R; 623/17.11–17.16
See application file for complete search history.

(56) References Cited

U.S. PATENT DOCUMENTS

| | | | | |
|---|---|---|---|---|
| 65,499 A * | 6/1867 | Miller | ......................... | 24/115 R |
| 643,238 A * | 2/1900 | Saeger | ............................ | 24/363 |
| 3,664,345 A * | 5/1972 | Dabbs et al. | .................. | 606/232 |
| 3,906,707 A * | 9/1975 | Morgan | ............................. | 54/35 |
| 4,128,100 A * | 12/1978 | Wendorff | ...................... | 606/141 |
| 4,507,618 A * | 3/1985 | Nelson | .......................... | 330/126 |
| 4,570,618 A * | 2/1986 | Wu | ............................... | 606/263 |
| 4,583,541 A * | 4/1986 | Barry | ............................. | 606/286 |
| 4,643,178 A | 2/1987 | Nastari et al. | | |
| 4,889,110 A * | 12/1989 | Galline et al. | ................ | 606/916 |
| 5,015,255 A | 5/1991 | Kuslich | | |
| 5,062,845 A | 11/1991 | Kuslich et al. | | |
| 5,219,359 A * | 6/1993 | McQuilkin et al. | ........... | 606/232 |
| 5,300,073 A | 4/1994 | Ray et al. | | |
| 5,417,690 A * | 5/1995 | Sennett et al. | .................. | 606/74 |
| 5,423,820 A | 6/1995 | Miller et al. | | |
| 5,445,639 A | 8/1995 | Kuslich et al. | | |
| 5,468,167 A * | 11/1995 | Givens | ........................... | 441/40 |
| 5,476,465 A * | 12/1995 | Preissman | ..................... | 606/279 |
| 5,484,437 A * | 1/1996 | Michelson | .................. | 606/86 A |
| 5,491,882 A | 2/1996 | Walston et al. | | |
| 5,496,318 A * | 3/1996 | Howland et al. | ............. | 606/249 |
| 5,507,823 A | 4/1996 | Walston et al. | | |
| 5,527,312 A * | 6/1996 | Ray | ............................... | 606/301 |
| 5,527,341 A * | 6/1996 | Gogolewski et al. | ......... | 606/232 |
| 5,571,191 A | 11/1996 | Fitz | | |
| 5,577,995 A | 11/1996 | Walker et al. | | |

(Continued)

*Primary Examiner* — Thomas C Barrett
*Assistant Examiner* — Matthew Lawson
(74) *Attorney, Agent, or Firm* — Kilpatrick Townsend & Stockton LLP

(57) ABSTRACT

A method for promoting fusion of and/or stabilizing a facet joint between two adjacent vertebrae comprises clamping the two adjacent vertebrae across the facet joint to apply a compressive force across the joint. Apparatus for promoting fusion of and/or stabilizing a facet joint comprises at least one cinchable tether and at least one locking member coupled with the tether for locking the cinched tether to maintain compressive force across the facet joint. The tether is adapted to extend through at least one hole through each of two adjacent vertebrae, across the facet joint.

28 Claims, 10 Drawing Sheets

LATERAL VIEW

U.S. PATENT DOCUMENTS

| | | | |
|---|---|---|---|
| 5,603,713 A | 2/1997 | Aust et al. | |
| 5,649,927 A * | 7/1997 | Kilpela et al. | 606/74 |
| 5,725,582 A * | 3/1998 | Bevan et al. | 606/263 |
| 5,741,261 A | 4/1998 | Moskovitz et al. | |
| 5,879,396 A | 3/1999 | Walston et al. | |
| 5,989,256 A * | 11/1999 | Kuslich et al. | 606/74 |
| 6,063,106 A * | 5/2000 | Gibson | 606/232 |
| RE36,758 E | 6/2000 | Fitz | |
| 6,117,160 A * | 9/2000 | Bonutti | 606/215 |
| 6,132,464 A | 10/2000 | Martin | |
| 6,200,322 B1 | 3/2001 | Branch et al. | |
| 6,277,120 B1 | 8/2001 | Lawson | |
| 6,312,431 B1 * | 11/2001 | Asfora | 606/279 |
| 6,423,088 B1 * | 7/2002 | Fenton, Jr. | 606/232 |
| 6,517,578 B2 | 2/2003 | Hein | |
| 6,540,747 B1 | 4/2003 | Marino | |
| 6,565,605 B2 | 5/2003 | Goble et al. | |
| 6,579,319 B2 | 6/2003 | Goble et al. | |
| 6,610,091 B1 | 8/2003 | Reiley | |
| 6,626,944 B1 | 9/2003 | Taylor | |
| 6,689,125 B1 | 2/2004 | Keith et al. | |
| 6,719,795 B1 * | 4/2004 | Cornwall et al. | 623/17.11 |
| 6,723,095 B2 * | 4/2004 | Hammerslag | 606/60 |
| 6,811,567 B2 | 11/2004 | Reiley | |
| 6,966,930 B2 * | 11/2005 | Arnin et al. | 623/17.11 |
| 7,004,970 B2 * | 2/2006 | Cauthen, III et al. | 623/17.16 |
| 7,074,238 B2 | 7/2006 | Stinson et al. | |
| 7,371,238 B2 * | 5/2008 | Soboleski et al. | 606/246 |
| 2002/0095154 A1 * | 7/2002 | Atkinson et al. | 606/61 |
| 2002/0107524 A1 | 8/2002 | Magana | 606/103 |
| 2002/0120270 A1 * | 8/2002 | Trieu et al. | 606/61 |
| 2003/0040746 A1 | 2/2003 | Mitchell et al. | |
| 2003/0105459 A1 * | 6/2003 | Songer | 606/61 |
| 2004/0111093 A1 | 6/2004 | Chappuis | |
| 2004/0127989 A1 | 7/2004 | Dooris et al. | |
| 2004/0254575 A1 * | 12/2004 | Obenchain et al. | 606/61 |
| 2005/0124993 A1 | 6/2005 | Chappuis | |
| 2005/0177240 A1 * | 8/2005 | Blain | 623/17.15 |
| 2005/0240188 A1 | 10/2005 | Chow et al. | |
| 2005/0276790 A1 | 12/2005 | Yamashita | |
| 2006/0190081 A1 | 8/2006 | Kraus et al. | |
| 2006/0235391 A1 | 10/2006 | Sutterlin, III | |
| 2007/0088358 A1 | 4/2007 | Yuan et al. | |
| 2008/0009866 A1 * | 1/2008 | Alamin et al. | 606/61 |

\* cited by examiner

POSTERIOR VIEW

SUPERIOR VIEW

LATERAL VIEW

FACET JOINT FUSION DEVICES AND METHODS

CROSS-REFERENCES TO RELATED APPLICATIONS

This application claims the benefit of provisional application 60/581,196, filed on Jun. 17, 2004, the full disclosure of which is incorporated herein by reference.

BACKGROUND OF THE INVENTION

The present invention relates to medical devices, methods and systems. More specifically, the invention relates to devices, methods and systems for promoting fusion of and/or stabilizing a facet joint of a spine.

Approximately 80% of Americans experience at least a single episode of significant back pain in their lifetime. For many people, back pain is a chronic, often debilitating disorder. The direct costs of treating back pain, as well as the indirect costs, such as lost wages and decreased productivity, are staggering.

Although back pain may be caused by a number of different factors, many cases of back pain are caused by conditions related to the spinal (or "vertebral") column. The vertebral column is made up of bones (vertebrae) and intervertebral discs that reside in the joint spaces between the vertebral bodies of the vertebrae. Three joints reside between every two adjacent vertebrae—one larger intervertebral joint between the two intervertebral bodies and two facet joints located posterolaterally relative to the vertebral bodies. These three joints share the load applied between every set of two vertebrae. Many spinal ailments are caused by degeneration, injury or deformity of these vertebral joints and/or intervertebral discs.

Treatment of spinal pain typically begins with conservative, non-surgical methods, such as rest, heat, analgesics, physical therapy and manipulation. Unfortunately, however, conservative treatments fail in a significant number of spinal pain patients, and surgery is often required. Current surgical procedures for treating intervertebral disc and joint maladies include decompressive surgery, in which all or part of an intervertebral disc and/or the spinal laminae and facets are removed, decompression with fusion of the joint (or "arthrodesis"), and arthrodesis alone. Intervertebral joint arthrodesis involves fusing two adjacent vertebrae to stop the motion between those vertebrae.

Decompression (removal of structures compressing the spinal nerves including laminae, facet joints and/or intervertebral discs) is a very common surgical procedure that is very effective in promptly relieving significant pain derived from pressure on spinal nerve roots ("radicular" pain). The overall success rates for decompression alone, however, range from 48% to 89%. Spinal fusion is sometimes needed in combination with decompression to more successfully treat spinal pain.

Intervertebral fusion is designed to stop the motion at a painful vertebral joint, which in turn should decrease pain generated from the joint. It is also performed to stabilize an unstable intervertebral segment, which if left unfused, could cause recurrent compression of the spinal nerves. Fusion procedures involve adding bone graft to an area of the spine to set up a biological response that causes the bone graft to grow between the two vertebral elements and thereby stop the motion at that segment. Often, some type of support structure is attached to the two vertebrae being fused, to hold the vertebrae in a stable position relative to one another while the bone graft material causes fusion. Typical support structures, for example, include bone screws (or "pedicle screws") attached to rods. Discectomy combined with fusion has been the most common surgical treatment for symptomatic cervical spondylosis for over 40 years. Good to excellent results have been reported in 52-100% of anterior lumbar interbody fusions and 50-95% of posterior lumbar interbody fusions.

A number of different spinal fusion surgical procedures are currently in use. The most common fusion procedure performed in lumbar surgery is posterolateral intertransverse fusion. Although the technique is often quite successful, the standard procedure often causes significant trauma to the paraspinous muscles. These muscles must be stripped from the transverse processes and retracted for an extended period of time to expose the underlying bone, which can result in denervation, devascularization, and ischemia of these important muscles, leading to atrophy and necrosis. Significant spasm in the short term and atrophy and necrosis in the long term contribute to the morbidity and sequelae of fusion. The clinical effect of this muscle morbidity can be significant postoperative pain and functional impairment in the convalescent period, as well as permanent impairment of paraspinal lumbar muscular function.

Other surgical techniques for performing spinal fusion are associated with similar and/or additional risk factors. For example, posterior lumbar interbody fusion ("PLIF") achieves fusion by inserting bone grafts, titanium threaded cages, bone dowels, or carbon fiber spacers filled with bone graft into an intervertebral disc space. All PLIF techniques require removal of the posterior bone of the spinal canal (laminectomy), retraction of the nerves and removal of the disc material from within the disc space, any of which may cause complications. Another procedure, anterior lumbar interbody fusion ("ALIF"), is similar to PLIF, except that in ALIF the disc space is fused by approaching the spine through the abdomen instead of through the back. An additional, and potentially significant, risk of ALIF is potential damage to abdominal structures, such as the large arteries that supply blood to the legs.

As mentioned above, with many spinal fusion procedures, some type of support structure, such as screws, rods, pins, cages and/or the like, is used to hold the adjacent vertebrae in place while they are fusing together with the help of the bone graft, bone adhesive, or the like. One of the primary risks of fusion surgery is that a solid fusion will not be obtained ("nonunion"), thus requiring further surgery. One of the main challenges of intervertebral fusion surgery is to stabilize the vertebrae long enough, using the support structure(s), so that they have time to fuse. Another challenge is actually applying the support structure properly. Pedicle screws, for example, may often be effective at providing support during intervertebral fusion, but they can be difficult to place properly, and if misplaced may cause nerve root and/or vascular injury.

As the population continues to age, surgical procedures for fusing and/or stabilizing vertebrae will become ever more common. Therefore, a need exists for improved techniques, devices and systems for performing such procedures. Such improved methods and devices should ideally facilitate and/or enhance intervertebral fusion, while preventing or reducing the prevalence of complications or sequelae. Ideally, minimally invasive procedures would be developed that would provide stabilization of an intervertebral joint for a sufficient period of time to allow the vertebrae to fuse. Also ideally, such procedures would be relatively simple to use. At least some of these objectives will be met by the present invention.

BRIEF SUMMARY OF THE INVENTION

Methods, devices and systems of the present invention promote fusion of and/or stabilize an intervertebral facet joint. Methods generally involve clamping two vertebrae across a facet joint to apply compressive force to the joint. Devices include one or more cinchable tethers, which in various embodiments may be passed through a hole extending through two vertebrae and/or may circumscribe the two vertebrae. Some embodiments also include one or more bone surface contacting members, such as plates, washers or the like, which enhance the ability of the cinchable tether to apply compressive force. One advantage of various embodiments of the invention is that they may be used to promote fusion and/or stabilization of one or more facet joints using a minimally invasive or less invasive procedure. In various embodiments, either percutaneous or open surgical approaches may be used. In a number of embodiments, techniques and devices of the invention may be used with other currently available devices or systems.

In one aspect of the present invention, a method for promoting fusion of a facet joint between two adjacent vertebrae involves clamping the two adjacent vertebrae across the facet joint to apply a compressive force across the joint. In some embodiments, the method further involves forming at least one hole through the two vertebrae across the facet joint. In such embodiments, clamping involves advancing a tether through the hole across the joint. Clamping may further involve cinching the tether to apply the compressive force, though cinching is not required in all embodiments.

In some embodiments, the hole extends through a first of the two vertebrae along a first axis and through a second of the two vertebrae along a second axis, so that advancing the tether through the hole causes the vertebrae to translate relative to each other. This "offset-hole" technique allows a surgeon to realign the vertebrae while also promoting fusion of and/or stabilizing the joint. In some embodiments, two holes are formed through the two vertebrae across the facet joint, and a separate tether is advanced through each of the two holes. Alternatively, two holes may be formed through the two vertebrae across the joint, and one tether may be advanced through both holes. In various other embodiments, any other suitable combination of holes and tether(s) may be used.

Optionally, a first bone surface contacting member slidably coupled with the tether may be contacted with a first of the two vertebrae, before the cinching step. The method may further comprise contacting a second bone surface contacting member slidably coupled with the tether with a second of the two vertebrae, also before the cinching step. One or more bone contacting members, such as plates, washers or the like, may help distribute force applied by the cinchable tether to more effectively apply compressive force across the joint.

The method may further include locking the cinched tether to maintain the compressive force across the facet joint. In some embodiments, two ends of the cinched tether overlap, and locking the cinched tether comprises locking the two ends together. For example, locking the two ends together may involve crimping at least one crimping member coupled with the two ends. In another embodiment, locking the two ends together involves locking two locking members together, each locking member being coupled with one of the two ends of the tether. In some embodiments, cinching and locking the tether(s) may be performed with the same tool, while in other embodiments separate tools may be used.

In some embodiments, rather than forming a hole through the vertebrae, clamping may involve circumscribing the joint with a tether disposed over the vertebrae. In some cases, such a tether may be cinchable for applying the compressive force. Optionally, the method may further include contouring external surfaces of the vertebrae to enhance engagement of the tether with the surfaces.

In yet another embodiment, clamping comprises engaging a clamping device with external surfaces of the vertebrae across the joint. Alternatively, clamping may comprise releasing a shape-memory or spring-loaded clamping device from constraint to clamp the vertebrae and apply the compressive force.

The method may optionally further include preparing at least one opposing surface of the two vertebrae, within the facet joint, by removing cartilage from the surface. Another optional step may include inserting at least one material into the facet joint to promote joint fusion. Such material(s) may include, for example, autologous bone, bone allograft, bone adhesive, bone morphogenic protein and/or bone growth promoting materials. In various embodiments, any of the above method steps may be performed percutaneously or as part of an open surgical procedure. The fusion promoter may optionally be placed in a reservoir or depot to provide controlled release over time and/or infusion of new bone growth into a matrix. The reservoir is appropriately shaped to fit the prepared surface. The reservoir might be made from known bioresorbable implantable materials, such as collagen, gelfoam, and copolymers of poly lactic and poly glycolic acid. Preparing the surface might involve removing cartilage and some of the bone at the surface to attain an appropriate geometry that fits the reservoir.

In another aspect of the present invention, a method for applying force across a facet joint between two vertebrae involves forming at least a first hole through the two vertebrae across the facet joint, advancing a first tether through the first hole across the joint, and cinching the tether. As with the above method, this technique may optionally further include contacting one or more bone surface contacting members slidably coupled with the tether with one or both of the two vertebrae. In one embodiment, two washers slidably disposed over the tether are contacted with surfaces of the two vertebrae outside the facet joint. The method may also include locking the cinched tether to maintain the force across the facet joint. Any of the features described above may be applied to this method, according to various embodiments.

In another aspect of the invention, a method for stabilizing a facet joint between two adjacent vertebrae comprises clamping the two adjacent vertebrae across the facet joint to apply a compressive force across the joint. Another alternative to stabilize the joint is to place an elastomer insert into a prepared surface (after removal of cartilage and some bone) and subsequently apply force to the joint to "sandwich" the elastomer insert. The insert is made from known implantable elastomers such as polyurethane or silicone. The elastomer insert allows some motion at the joint. Again, any of the features described above may be applied to this method.

In another aspect of the present invention, apparatus for promoting fusion of a facet joint between two adjacent vertebrae comprises at least one cinchable tether adapted to extend through at least one hole through each of two adjacent vertebrae across the facet joint and at least one locking member coupled with the tether for locking the cinched tether to maintain compressive force across the facet joint. Some embodiments further include at least a first bone surface contacting member slidably coupled with the tether for contacting a first of the two vertebrae external to the facet joint. The apparatus may further include a second bone surface contacting member coupled with the tether for contacting a second of the two vertebrae external to the facet joint. In such embodiments, cinching the tether applies compressive force between the first and second bone surface contacting members across the facet joint.

In some embodiments, each of the first and second bone surface contacting members comprises a plate having at least one hole allowing for passage of the tether. Some embodiments include two cinchable tethers, and each plate includes two holes allowing for passage of the two tethers. Optionally, the plates may be curved to conform to surfaces of the two vertebrae. In some embodiments, the plates are malleable to conform to surfaces of the two vertebrae. Alternatively, the plates may be completely rigid, or each plate may include a rigid portion and a malleable portion for contacting a surface of one of the vertebrae. Any suitable materials may be used to manufacture the plates, such as but not limited to titanium, titanium alloys, stainless steel, cobalt-chromium alloy, carbon filled PEEK, ultra-high molecular weight polyethylene, silicone, polyurethane, SEBS-based materials and/or the like. (SEBS-based materials are a family of thermoplastic synthetic rubber materials, with SEBS standing for styrene-ethylene-butadiene-styrene). In some embodiments, the apparatus may be made predominantly of radiolucent materials, with one or more radiopaque markers facilitating visualization of the device. In other embodiments, the apparatus (or one or more parts of the apparatus) may be made of radiopaque materials.

Some embodiments include a curved bone contacting member adapted to wrap around surfaces of the two vertebrae adjacent the facet joint. In these embodiments, cinching the tether compresses the curved bone contacting member to apply compressive force across the facet joint. Optionally, at least part of the bone contacting member may be malleable to conform to the surfaces of the two vertebrae.

The tether (or tethers) may have any suitable length, diameter, configuration or the like, and may be made of any suitable material or combination of materials. In some embodiments, for example, the tether may comprise a cord, cable, suture, wire, T-tag or the like. Materials used to form a tether may include, but are not limited to, stainless steel, cobalt-chromium alloy, titanium, Nitinol, ultra-high molectular weight polyethylene, cobalt-chromium alloy, PTFE, PET and/or the like.

Similarly, the locking member (or multiple locking members) may have any suitable size, shape and configuration and may be made of any suitable material(s). In one embodiment, the locking member comprises at least one crimping member coupled at or near both ends of the tether and slidable along at least one end of the tether. In another embodiment, the locking member comprises a T-tag. In yet another embodiment, the locking member comprises at least a first locking member coupled with the tether at or near a first end of the tether and at least a second locking member coupled with tether at or near a second end of the tether, wherein the first and second locking members lock together. In another embodiment, locking member comprises a lasso member coupled with one end of the tether and a rivet slidably coupled with the tether and adapted to engage and lock with the lasso.

In another aspect of the present invention, a clamping device for stabilizing a facet joint between two adjacent vertebrae includes at least one bone surface contacting member for engaging at least one of the two vertebrae and at least one cinchable tether slidably coupled with the bone surface contacting member and passable through a hole extending through each of the two vertebrae, across the facet joint. The cinchable tether and the bone surface contacting member are adapted to apply compressive force across the facet joint. In various embodiments, this apparatus may have any of the features described above.

In yet another aspect of the present invention, a system for promoting fusion of a facet joint between two adjacent vertebrae includes a facet joint clamping device and a drill for forming the at least one hole through the two vertebrae. The facet joint clamping device includes at least one cinchable tether adapted to extend through at least one hole through each of two adjacent vertebrae, across the facet joint. Optionally, the clamping device may further include any of the device features described above.

In some embodiments, the clamping device, the drill or both are calibrated to form the at least one hole through the vertebrae so as to realign the two vertebrae when the cinchable tether is passed therethrough. The system may optionally further include an access device for providing access to the two vertebrae. In various embodiments, the access device may provide for percutaneous access or open surgical access to the two vertebrae.

The system may also include one or more bone preparation devices for preparing one or more bone surfaces within the joint by removing at least one of cartilage or bone. In one embodiment, for example, a bone preparation device comprises a flexible cutting guide and a cutting device passable over the cutting guide, with the guide and the cutting device adapted to remove cartilage from the bone surfaces while minimizing removal of bone. In some embodiments, the system further includes at least one fusion promoting material adapted for insertion into the joint to promote fusion of the joint.

These and other aspects and embodiments of the invention are described further below with reference to the drawing figures.

BRIEF DESCRIPTION OF THE DRAWING FIGURES

DETAILED DESCRIPTION OF THE INVENTION

Figure 1:
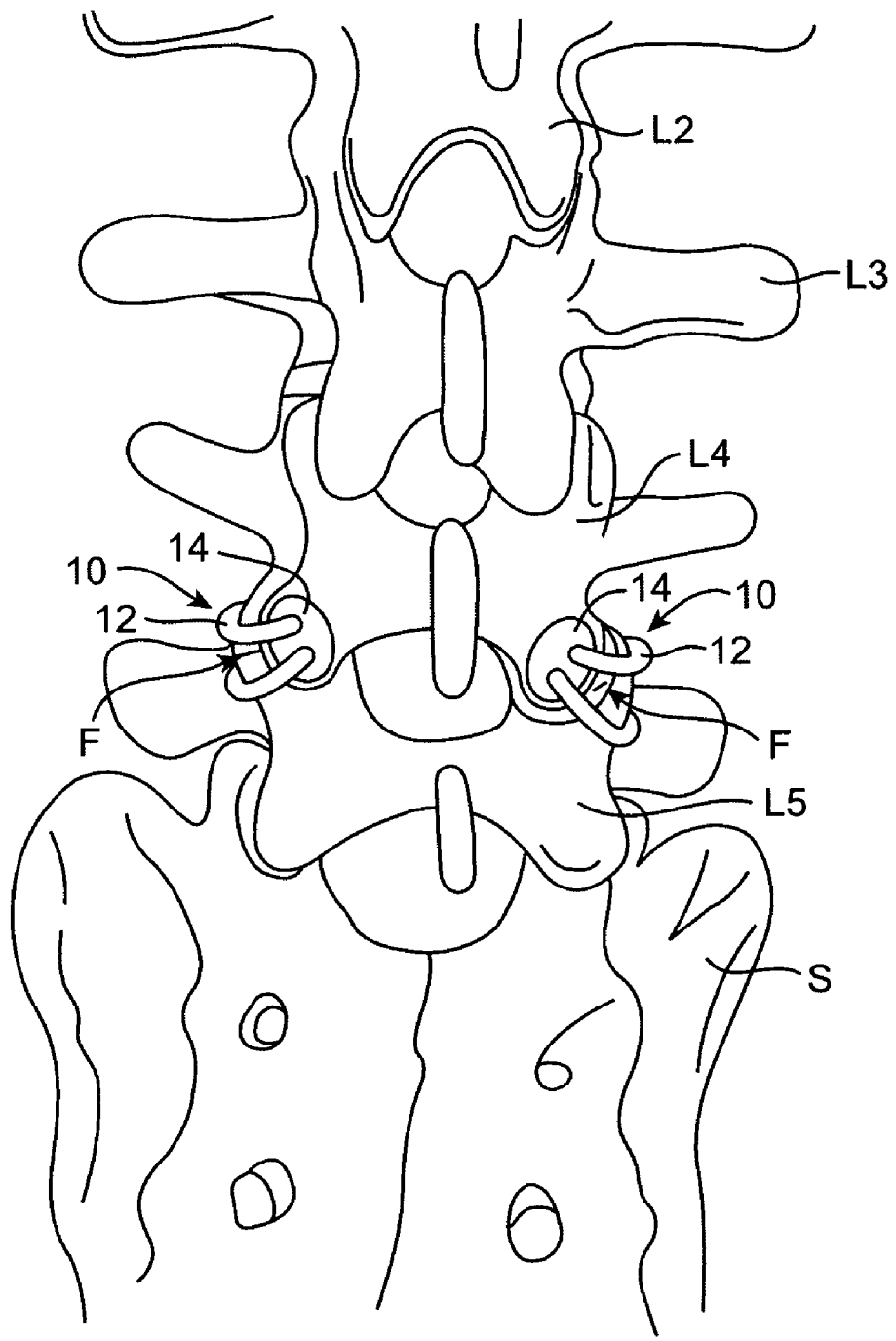
FIG. 1 is a posterior perspective view of a lumbar portion of a vertebral column, with fusion/stabilization devices attached across two facet joints according to one embodiment of the present invention.

FIG. 1 is a posterior perspective view of the most inferior four lumbar vertebrae (L2-L5) and a portion of the sacrum S. Attached across the two facet joints F between the L4 and L5 vertebrae is a clamping device 10 according to one embodiment of the present invention. Each clamping device 10 includes a tether 12 and two bone surface contacting members 14 (only one contacting member 14 is visible for each device 10 in FIG. 1.) As is described in further detail below, two holes are drilled through each of the facet joints F of L4 and L5, tethers 12, coupled with bone contacting members 14, are passed through the holes, and tethers 12 are cinched to apply compressive force across the facet joints F, thus promoting fusion of and/or stabilizing the joints F.

Figure 2:
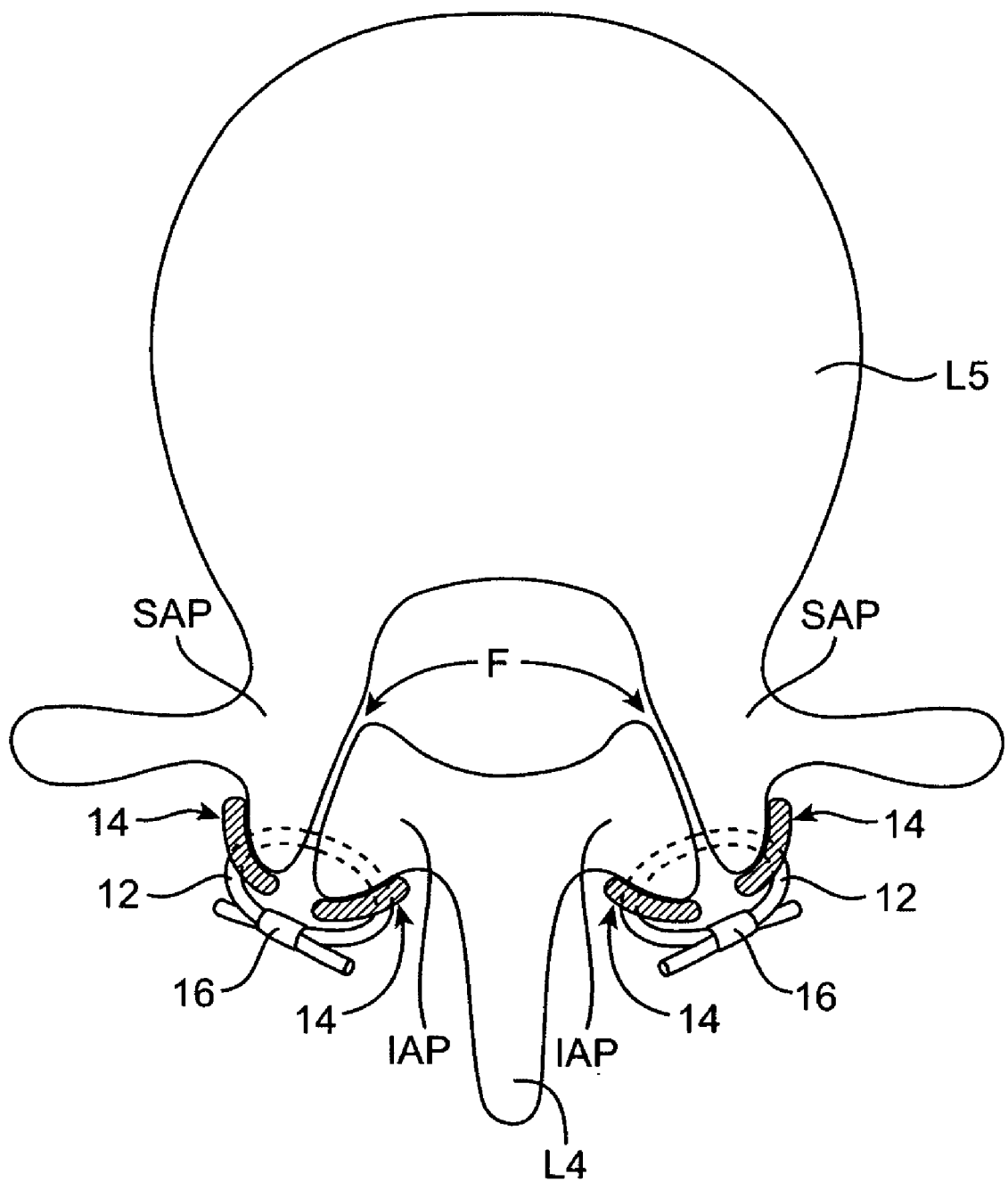
FIG. 2 is a superior view of a lumbar vertebra and part of an adjacent vertebra, with the fusion/stabilization device of FIG. 1 attached across the facet joints.
Figure 3:
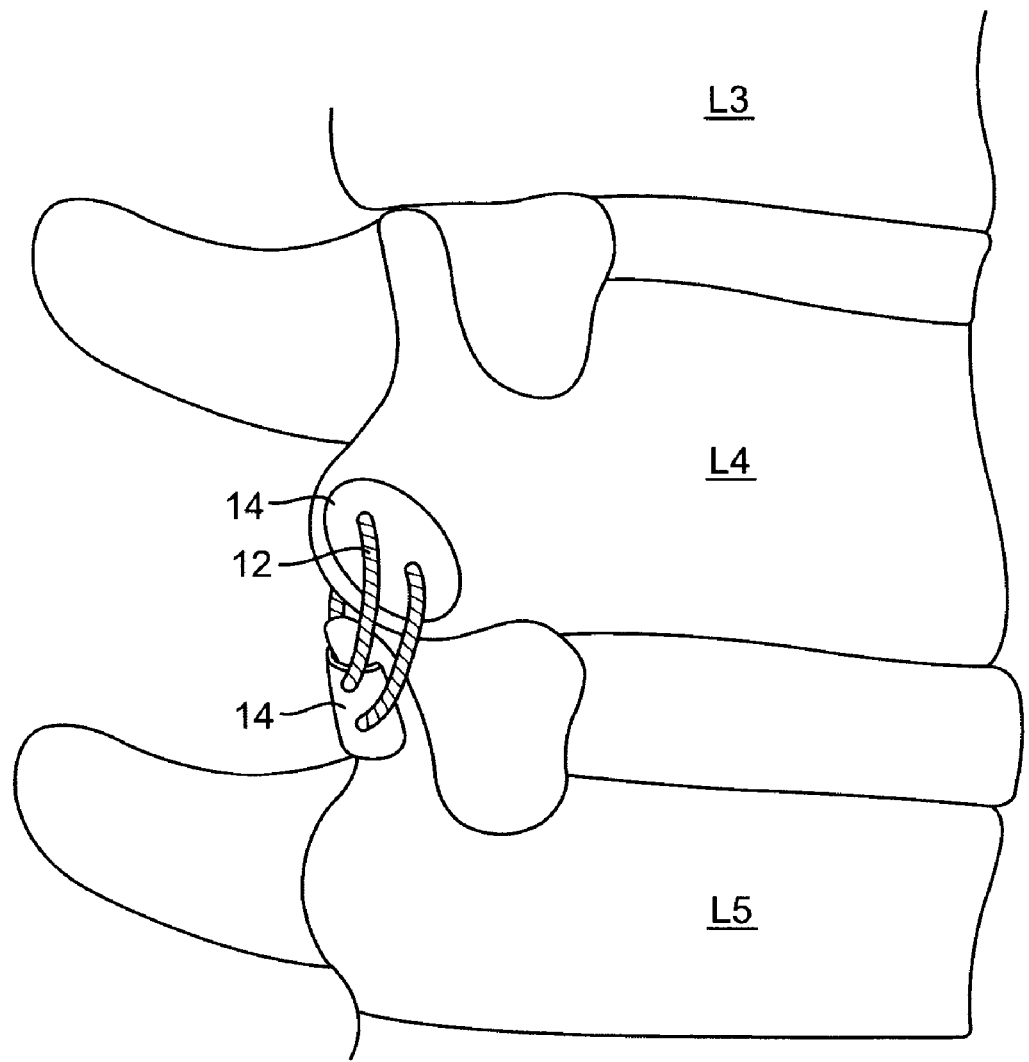
FIG. 3 is a lateral view of two adjacent vertebrae, with the fusion/stabilization device of FIG. 1 attached across the facet joints.

FIGS. 2 and 3 provide superior and lateral views, respectively, of clamping device 10 from FIG. 1. In FIG. 2, it can be seen that tethers 12 extend through holes (dotted lines) in the vertebrae L4, L5 and across the facet joints F. Typically, the holes are drilled or otherwise formed through the superior articular process SAP of the inferior vertebrae (in this case L5) and through the inferior articular process IAP of the superior vertebrae (in this case L4). Of course, clamping device 10 may be applied across one or more facet joints of any two vertebrae, and its use is in no way limited to lumbar vertebrae or any other vertebrae. Additionally, if holes are formed to apply clamping device 10, they may be formed through any suitable part of adjacent vertebrae in order to cross the facet joints F, and in various embodiments such holes may pass through only one articular process, or through neither articular process.

Once tether 12 is passed through one or more holes in two vertebrae L4, L5 and bone surface contacting members 14 are engaged with vertebral bone, tether 12 is typically cinched, to apply compressive force against the facet joint F, and locked, to maintain the force. Thus, clamping device 10 may suitably include one or more locking members 16 for locking the cinched tether 12. Locking member 16 may comprise any suitable device for maintaining the force of cinched tether, as will be described in further detail below.

In various embodiments, each bone surface contacting member 14 may include one aperture or hole for passage of tether 12, two holes, or more than two holes. Furthermore, clamping device 10 may include one tether 12 or multiple tethers 12, in various embodiments. In the embodiment shown in FIGS. 1-3, one tether 12 extends through both holes on the two bone surface contacting members 14 of each device 10.

Figure 4:
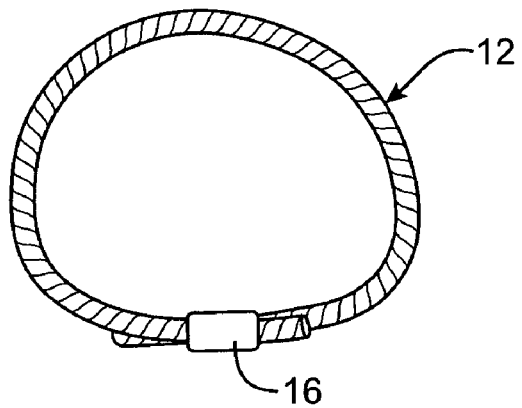
FIG. 4 is a perspective view of a clamping device including a tether and locking member, according to one embodiment of the present invention.
Figure 4B:
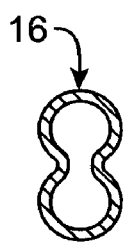
FIGS. 4A and 4B are perspective and end-on views, respectively, of the locking member of FIG. 4.
Figure 4A:
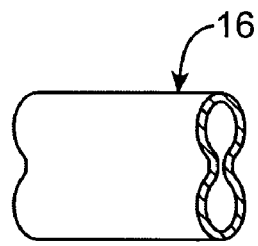

Referring now to FIG. 4, one embodiment of a tether 12, slidably coupled with a locking member 16, is shown. Locking member 16 is shown in greater detail in FIGS. 4A and 4B. In various embodiments, tether 12 may be made of any of a number of suitable materials, such as but not limited to stainless steel, cobalt-chromium alloy, titanium, Nitinol, ultra-high molecular weight polyethylene, cobalt-chromium alloy, PTFE or PET. Locking member 16 may similarly be made of any suitable material. In one embodiment, locking member 16 made of a material that allows it to be crimped to lock the two ends of tether 12. In various embodiments, locking member 16 may be fixedly attached to one end of tether and slidable over the other end, or may be slidable over both ends of the tether. Generally, locking member may have any suitable shape, size or configuration, according to various embodiments.

Figure 5:
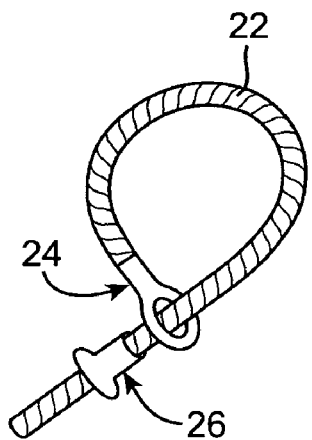
FIG. 5 is a perspective view of a clamping device including a tether and locking members according to another embodiment of the present invention.

For example, and with reference now to FIG. 5, in one embodiment a tether 22 is coupled at one end with a lasso-like circular locking member 24, and a rivet 26 is slidably disposed over the other end of tether 22. Rivet 26 may be advanced over tether 22 into the opening of circular member 24, and circular member 24 may then be crimped down to lock over rivet 26. Alternatively, rivet 26 may be sized to lock within circular member 24 without crimping. In various embodiments, any other suitable locking member(s) may be included, such as T-tags, snap-fit locking members, pressure-fit members or the like.

Figure 6:
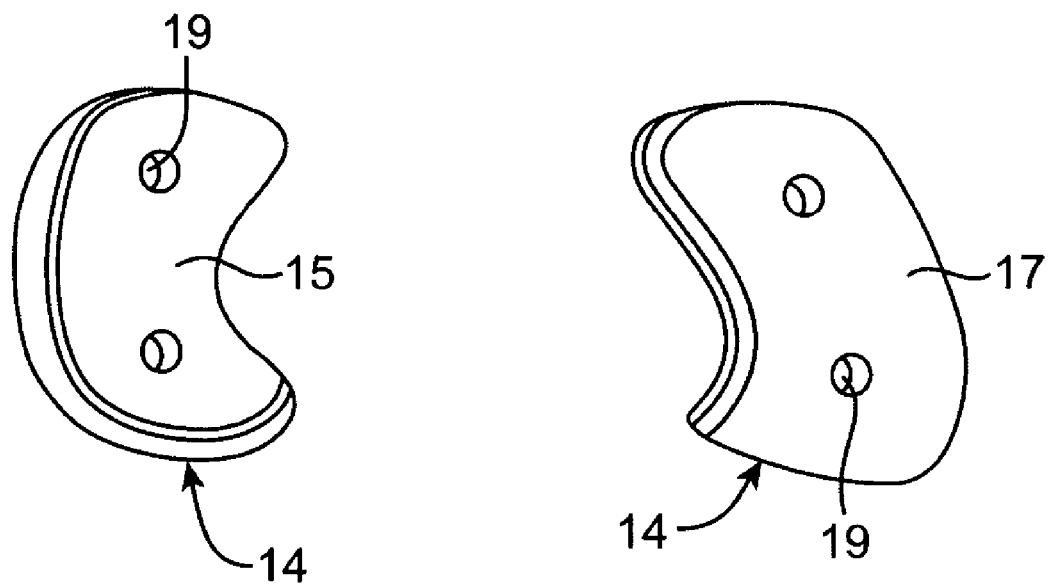
FIG. 6 is a perspective view of two bone surface contacting members according to one embodiment of the present invention.

Referring now to FIG. 6, bone surface contacting members 14 may have any suitable shape, size and configuration and may be made of any suitable material or combination of materials. In some embodiments, contacting members 14 are completely rigid, while in other embodiments they may be partly or completely malleable. As illustrated in FIG. 6, some embodiments include a rigid outer layer 17 or shell coupled with a malleable inner layer 15 for contacting bony surfaces of vertebrae. Examples of materials from which bone surface contacting members 14 may be constructed include, but are not limited to, titanium, titanium alloys, stainless steel, cobalt-chromium alloy, carbon filled PEEK, ultra-high molecular weight polyethylene, silicone, polyurethane and SEBS-based materials. Contacting members 14 may have two apertures 19 for slidably passing along tether 12, or may have one aperture 19 or any other suitable number.

Figure 6A:
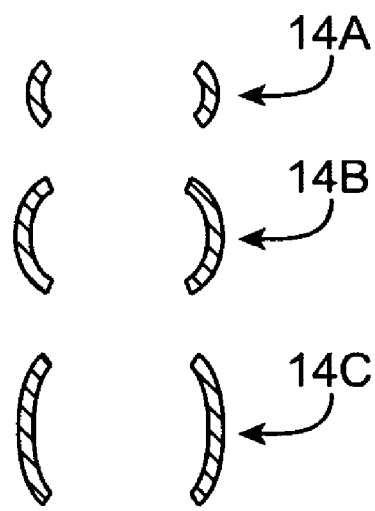
FIG. 6A are end-on views of three sizes of bone surface contacting members according to three different embodiments of the present invention.

As illustrated in FIG. 6A, in various embodiments bone surface contacting members 14A-14C may have any of a number of suitable sizes and shapes. In one embodiment, a number of differently shaped contacting members 14A-14C may be provided in a kit, so that members 14A-14C may be selected based on the size and shape of the vertebrae on which they are to be placed. In alternative embodiments, contacting members 14 may be formed as washers, plates or the like, and may be flat or curved. In one embodiment, a single curved plate is used, rather than two contacting members 14, the curved plate adapted to wrap around two vertebrae adjacent the facet joint.

Figure 7:
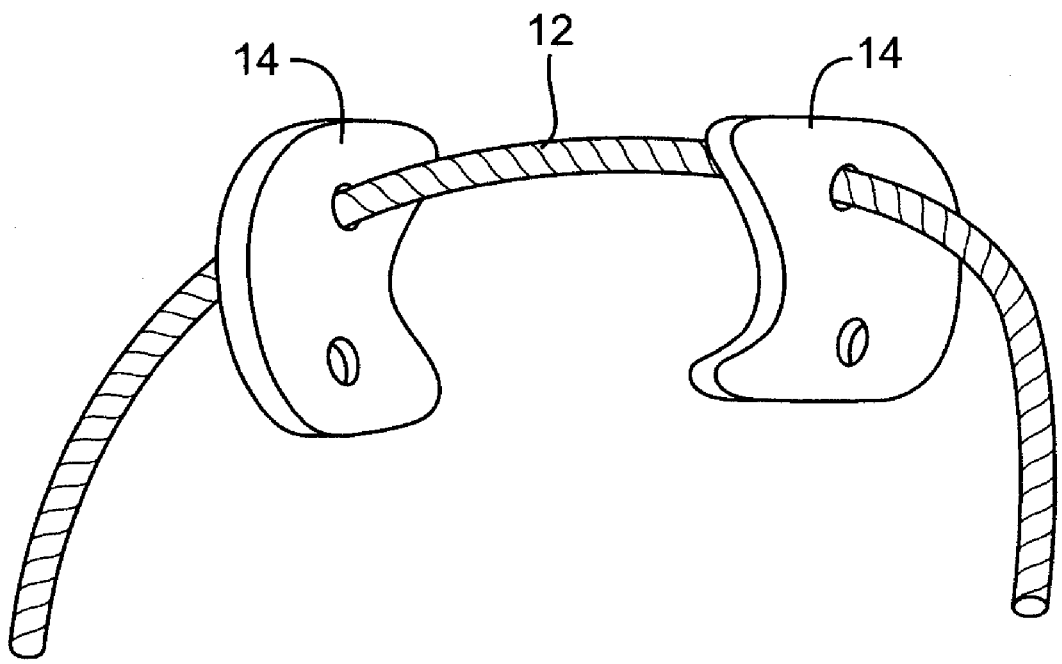
FIG. 7 is a perspective view of a portion of a tether extending through apertures on two bone surface contacting members according to one embodiment of the invention.

FIG. 7 shows tether 12 extending through two bone surface contacting members 14. Again, in various embodiments, multiple tethers 12 may be used, one, two or any suitable number of contacting members 14 may be used, and/or the like.

In an exemplary method for using clamping device 10 to promote facet joint fusion and/or stabilization, a first step involves gaining access to the facet joint(s) to be fused/stabilized. Access may be gained via any suitable technique and route, using any suitable devices or systems. For example, some suitable access methods will be minimally invasive and percutaneous, while others may involve open surgical approaches. In some embodiments, currently available minimally invasive access systems, such as the MAST™ system provided by Medtronic, Inc. or the ATAVI™ system provided by Endius, Inc. may be used.

Once access is gained, some embodiments involve preparing the surfaces of the facet joint by removing cartilage. In alternative embodiments, currently available devices, such as curettes, may be used for such preparation, or specialized facet joint preparation devices, such as a flexible cutting guide and a cutter, may be used. One or more holes may then be formed through adjacent vertebrae across the facet joint(s). Holes may be formed using currently available drilling devices, such as the CurveTek™ bone tunneling system provided by Arthrotek, Inc., or alternatively by any other suitable device(s). In some instances, a hole may be formed so that it is offset through one vertebra relative to the adjacent vertebra. When tether 12 is then extended through the offset holes and cinched, the facets translate relative to one another, thus realigning the joint. Thus, in some embodiments, realignment as well as fusion/stabilization may be achieved. Some embodiments include jigs, calibrations and/or the like to facilitate offsetting of holes between vertebrae.

Once the holes are formed in two adjacent vertebrae, one or more tethers 12 are passed through the holes. One or more bone surface contacting members 14 may be passed along each tether 12 to contact the vertebrae. Tether 12 is then cinched and locked with one or more locking members 16 to apply and maintain compressive force across the joint.

If joint fusion is desired, at any suitable point in the process one or more joint fusion materials may be placed in the joint, between the two articular surfaces. Such materials may include, for example, autologous bone, bone allograft, bone adhesive, bone morphogenic proteins and/or bone growth promoting material(s).

Figure 8:
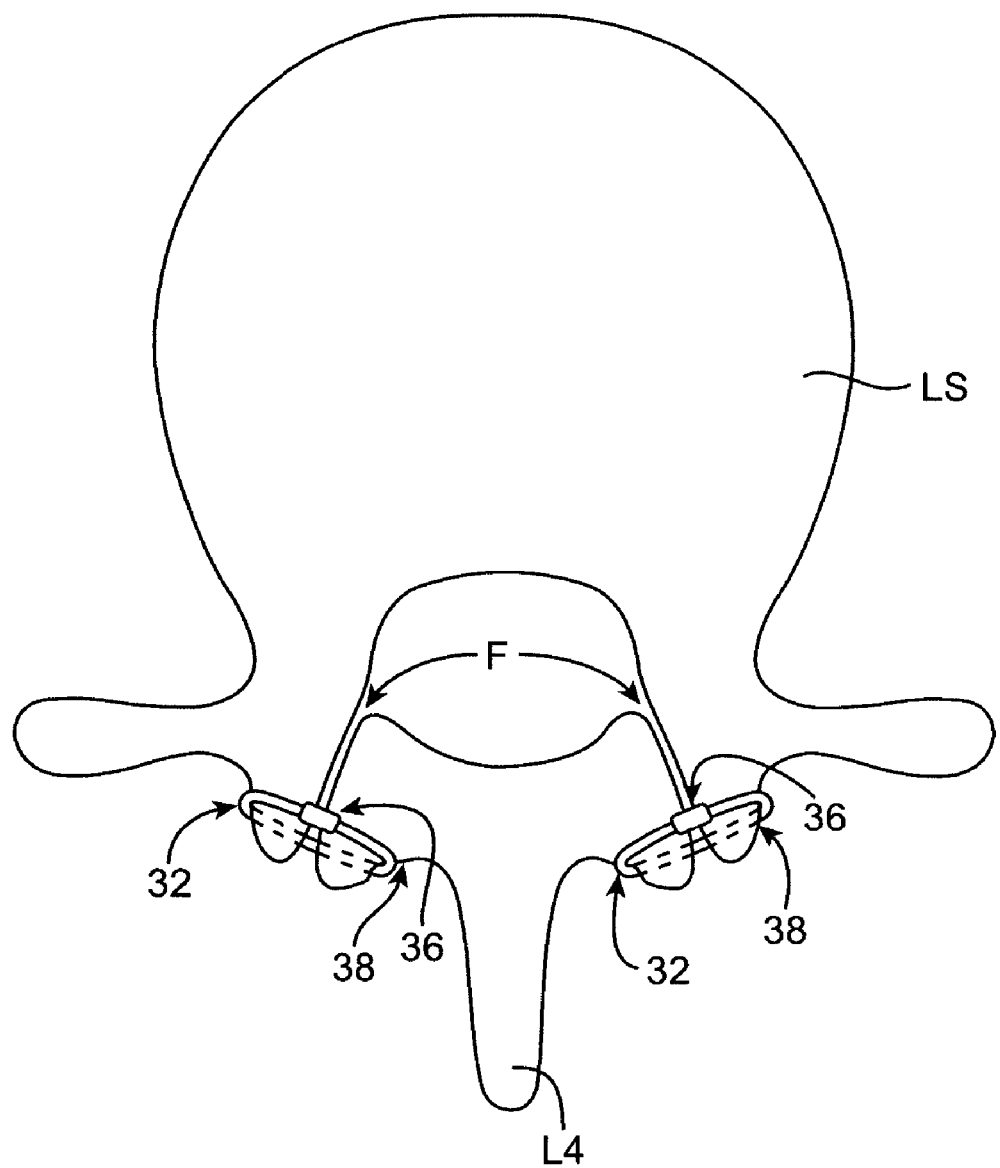
FIG. 8 is a superior view of a lumbar vertebra and part of an adjacent vertebra, with a fusion/stabilization device applied to two facet joints according to another embodiment of the invention.

Referring now to FIG. 8, in an alternative embodiment of the invention, no holes are placed through the vertebrae. Instead, one or more tethers 32 are wrapped or circumscribed around the vertebrae adjacent the facet joint F and then cinched to apply compressive force across the joint. Tethers 32 may be coupled with one or more locking members 36 to retain force across the joint F. In various embodiments, bone surface contacting members may or may not be used. Some embodiments further include preparing external surfaces of the vertebrae to enhance engagement of tether(s) 12 with the vertebrae, for example by forming one or more troughs 38 or paths for holding tether(s) 12.

Figure 9:
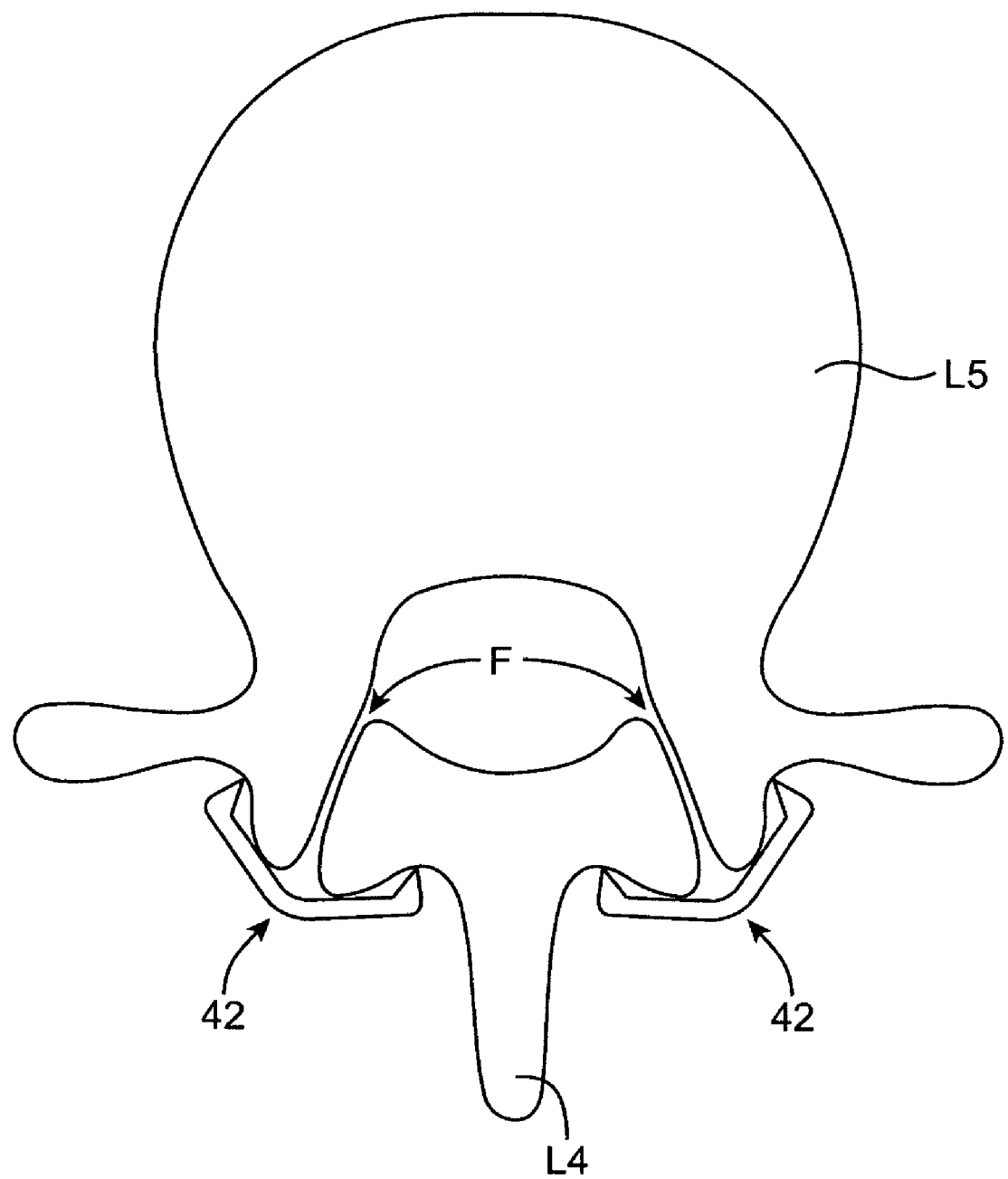
FIG. 9 is a superior view of a lumbar vertebra and part of an adjacent vertebra, with a fusion/stabilization device applied to two facet joints according to another embodiment of the invention.

Referring to FIG. 9, another embodiment may involve releasing a shape-memory or spring-loaded clamping device 42 from constraint to engage the vertebrae adjacent a facet joint F and to apply compressive force across the joint. Clamping device 42 may be made of any suitable shape-memory material, such as Nitinol, or may be spring loaded in a delivery device.

Figure 10:
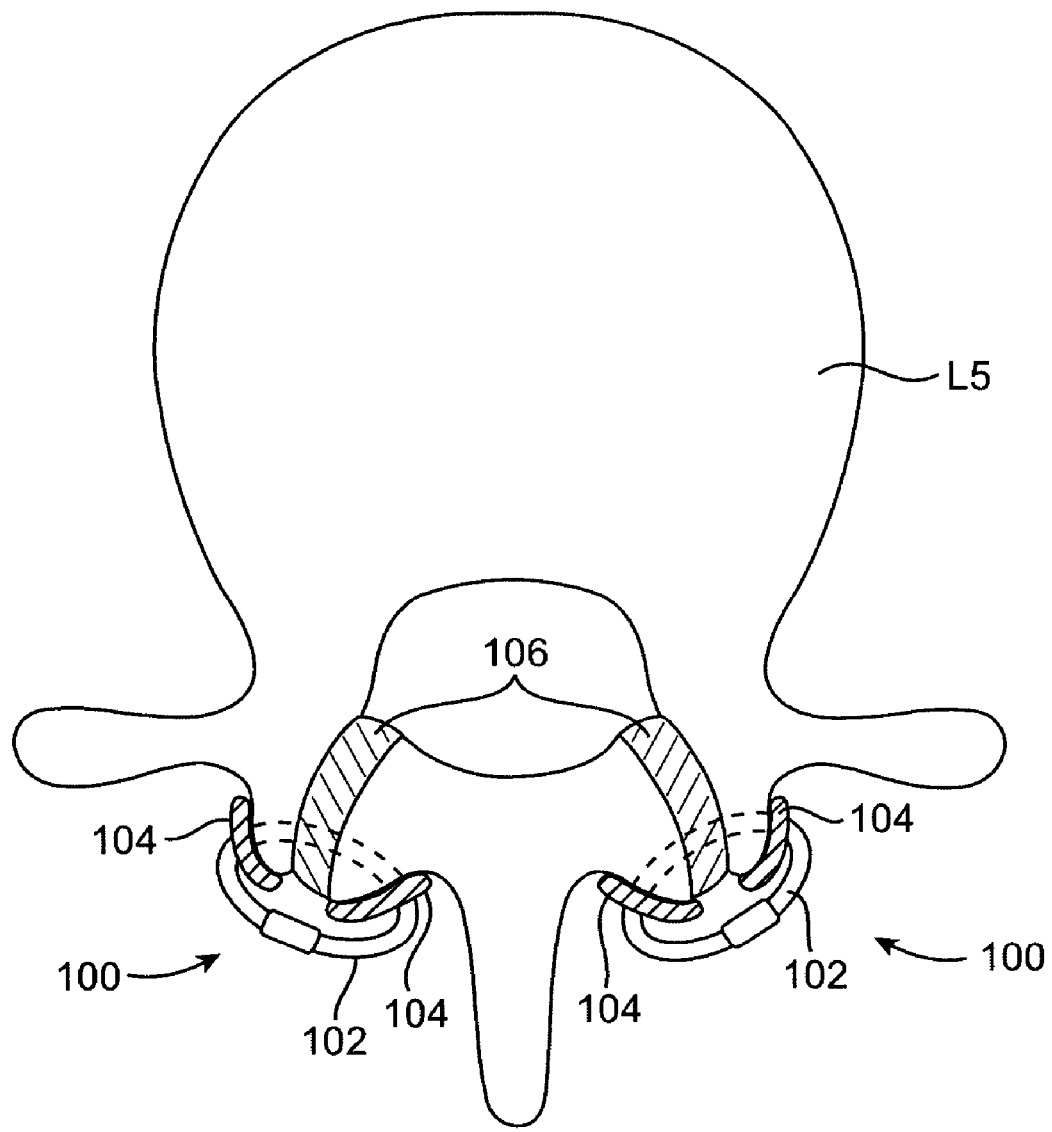
FIG. 10 illustrates an elastomeric insert for facet joint fusion.
Figure 11A:
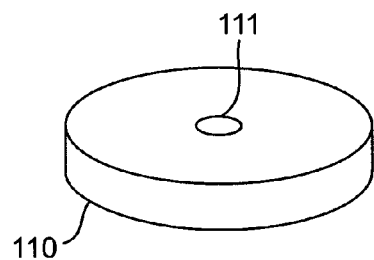
FIGS. 11A-11E illustrate alternative embodiments of elastomeric inserts and reservoirs for facet joint fusion.
Figure 11B:
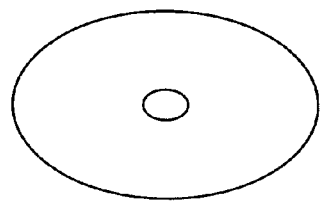
Figure 11C:
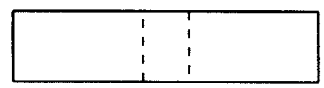
Figure 11D:
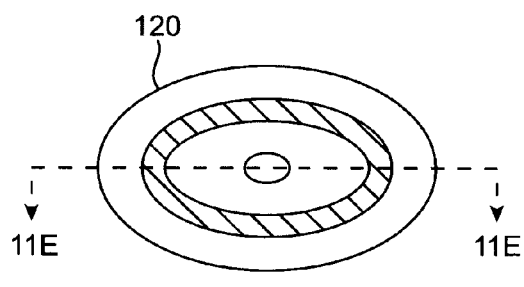
Figure 11E:
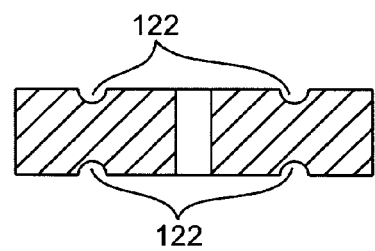

FIG. 10 shows a superior view of the facets with inserts 100 at the joints which are held together by tethers 10 and washers. The insert may comprise a reservoir 106 which optionally includes or provides an elastomeric insert. FIGS. 11A-11E show two embodiments of the reservoir/elastomer insert. The first embodiment shows an insert 110 with a central hole 112 to pass a tether through. The number of holes depends on the number of tethers. If the insert is a reservoir then it would be made of a bioresorbable material. The insert 110 is made from an elastomer in instances where the joint is being stabilized but not fused. The second embodiment 120 (FIGS. 11D and 11E) includes a channel 122 on both surfaces of the insert that face the bone. The channel 122 serves as a reservoir for fusion enhancing substances as an alternative to sponge-like bioresorbable matrices.

Although the foregoing is a complete and accurate description of the present invention, a number of various additions, changes or the like may be made to various embodiments described above without departing from the scope of the invention. Therefore, the description above is provided primarily for exemplary purposes and should not be interpreted to limit the scope of the invention as it is set forth in the claims.

What is claimed is:

1. A method for promoting fusion of a facet joint between two processes having opposing surfaces on adjacent vertebrae, the method comprising:
   preparing at least one of the opposing surfaces of the two processes of the facet joint, within the facet joint, by removing cartilage from the at least one surface; and
   clamping the facet joint including a superior articular process (SAP) of an inferior vertebra and an inferior articular process (IAP) of a superior vertebra to apply a compressive force across the facet joint, wherein the compressive force promotes fusion of the facet joint wherein clamping comprises engaging plates against the surfaces of each process, wherein the plates have curved surfaces which conform to the surfaces of the processes.

2. A method as in claim 1, further comprising forming at least one hole through the articular processes of the facet joint, wherein clamping comprises advancing a tether through the hole across the facet joint to hold the plates together to apply compressive forces across the facet joint.

3. A method as in claim 2, further comprising forming two holes through the articular processes of the facet joint, wherein a separate tether is advanced through each of the two holes and both of the plates.

4. A method as in claim 2, further comprising forming two holes through the articular processes of the facet joint, wherein the tether is advanced through both holes.

5. A method as in claim 2, wherein clamping further comprises cinching the tether.

6. A method as in claim 5, wherein the at least one hole extends through a first of the two processes of the facet joint along a first axis and through a second of the two processes along a second axis, and wherein advancing the tether through the hole causes the processes to translate relative to each other.

7. A method as in claim 5, further comprising, before the cinching step, contacting at least a first bone surface contacting member slidably coupled with the tether with a first of the processes of the facet joint.

8. A method as in claim 7, further comprising contacting a second bone surface contacting member slidably coupled with the tether with a second of the processes of the facet joint.

9. A method as in claim 5, further comprising locking the cinched tether to maintain the compressive force across the facet joint.

10. A method as in claim 9, wherein two ends of the cinched tether overlap, and wherein locking the cinched tether comprises locking the two ends together.

11. A method as in claim 10, wherein locking the two ends together comprises crimping at least one crimping member coupled with the two ends.

12. A method as in claim 10, wherein locking the two ends together comprises locking two locking members together, wherein each locking member is coupled with one of the two ends.

13. A method as in claim 1, further comprising inserting at least one material into the facet joint to promote joint fusion.

14. A method as in claim 13, wherein the material is selected from the group consisting of autologous bone, bone allograft, bone adhesive, bone morphogenic protein and bone growth promoting materials.

15. A method as in claim 1, wherein clamping is performed percutaneously.

16. A method as in claim 1, wherein clamping is performed as part of an open surgical procedure.

17. A method of applying force across a facet joint between two vertebrae, the method comprising:
- forming at least a first hole through a superior articular process (SAP) of an inferior vertebra and through an inferior articular process (IAP) of a superior vertebra, across the facet joint;
- preparing at least one opposing surface of the two processes of the facet joint, within the facet joint, by removing at least one of cartilage and bone from the surface;
- engaging a first plat against a superior surface of the IAP and a second plate against an inferior surface of the SAP, wherein the plates conform to the surfaces of the processes and have a first hold which aligns with the first hole in the SAP and the IAP;
- advancing a first tether through the first holes and across the joint; and
- cinching the first tether;
- forming at least a second hold through the two processes of the facet joints across the joint wherein second holes in the plates align with the second hole in the processes;
- advancing a second tether through the second holes and across the joint; and
- cinching the second tether.

18. A method as in claim 17, further comprising locking the cinched tethers to maintain the force across the facet joint.

19. A method as in claim 17, further comprising inserting at least one material into the facet joint to promote joint fusion.

20. A method as in claim 19, wherein the material is selected from the group consisting of autologous bone, bone allograft, bone adhesive, bone morphogenic proteins and bone growth promoting materials.

21. A method as in claim 2, wherein the hole is initially offset between the articular processes, wherein cinching the tether realigns the hole and the facet joint.

22. A method as in claim 17, further comprising preparing the surfaces of the facet joint by removing cartilage prior to cinching.

23. A method as in claim 17, wherein the hole is initially offset between the articular processes, wherein cinching the tether realigns the hole and the facet joint.

24. A method for applying force across a facet joint between two vertebrae, the method comprising:
- forming at least a first hole through a superior articular process (SAP) of an inferior vertebra and through an inferior articular process (IAP) of a superior vertebra, across the facet joint between two processes having opposing surfaces on adjacent vertebrae;
- preparing at least one of the opposing surfaces of the two processes of the facet joint, within the facet joint, by removing at least one of cartilage and bone from the surface;
- engaging a first plate against a superior surface of the IAP and a second plate against an inferior surface of the SAP, wherein the plates conform to the surfaces of the processes and have a first hole which aligns with the first hole in the SAP and IAP;
- advancing a first tether through the first holes and across the joint; and
- cinching the tether.

25. A method as in claim 24, further comprising locking the cinched tether to maintain the force across the facet joint.

26. A method as in claim 24, further comprising:
- forming at least a second hole through the two processes of the facet joint across the joint wherein second holes in the plates align with the second hole in the processes; and
- advancing a second tether through the second holes and across the joint; and
- cinching the second tether.

27. A method as in claim 24, further comprising inserting at least one material into the facet joint to promote joint fusion.

28. A method as in claim 27, wherein the material is selected from the group consisting of autologous bone, bone allograft, bone adhesive, bone morphogenic proteins and bone growth promoting materials.

* * * * *